United States Patent [19]

Girard et al.

[11] Patent Number: 5,093,356

[45] Date of Patent: Mar. 3, 1992

[54] INDENYL HYDROXAMIC ACIDS AND HYDROXY UREAS AS INHIBITORS OF 5-LIPOXYGENASE

[75] Inventors: Yves Girard, Ile Bizard; Pierre Hamel, Vimont; Daniel Delorme, St. Lazare, all of Canada

[73] Assignee: Merck Frosst Canada, Inc., Quebec, Canada

[21] Appl. No.: 465,295

[22] Filed: Jan. 16, 1990

[51] Int. Cl.⁵ ............... C07C 259/04; A61K 31/19; C07D 333/22; C07D 307/02
[52] U.S. Cl. .................... 514/438; 514/471; 514/575; 549/77; 549/496; 562/621; 562/622; 562/623
[58] Field of Search ............ 562/623, 622, 621; 549/77, 496; 514/575, 438, 471

[56] References Cited

U.S. PATENT DOCUMENTS

| | | | |
|---|---|---|---|
| 3,312,730 | 4/1967 | Winter et al. | 260/473 |
| 3,647,858 | 3/1972 | Hinkley et al. | 260/470 |
| 3,654,349 | 4/1972 | Shen et al. | 260/515 M |
| 3,692,651 | 9/1972 | Sletzinger et al. | 204/158 R |
| 3,732,292 | 5/1973 | Hinkley et al. | 260/515 A |
| 3,737,455 | 6/1973 | Shen et al. | 260/520 |
| 3,759,987 | 9/1973 | Conn et al. | 260/515 A |
| 3,819,716 | 6/1974 | Shen et al. | 260/607 A |
| 3,822,310 | 7/1974 | Shen et al. | 260/515 A |
| 3,932,498 | 1/1976 | Shen et al. | 260/515 A |
| 4,705,782 | 11/1987 | Logan et al. | 562/622 |
| 4,738,986 | 4/1988 | Kneen et al. | 562/622 |

FOREIGN PATENT DOCUMENTS

| | | |
|---|---|---|
| 0206241 | 6/1986 | European Pat. Off. |
| 0279263 | 2/1988 | European Pat. Off. |
| 87/04152 | 12/1986 | PCT Int'l Appl. |
| 2191194A | 6/1987 | United Kingdom |

*Primary Examiner*—Joseph E. Evans
*Attorney, Agent, or Firm*—William H. Nicholson; Raymond M. Speer; Gabriel Lopez

[57] ABSTRACT

Compounds having the formula I:

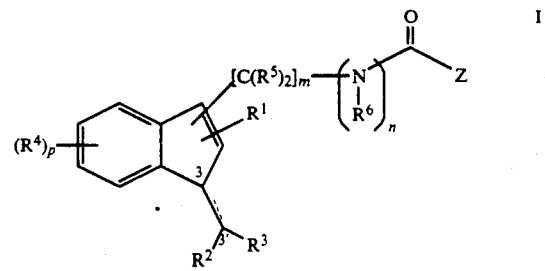

are inhibitors of the 5-lipoxygenase enzyme. These compounds are useful as anti-asthmatic, anti-allergic, anti-inflammatory, and cytoprotective agents. They are also useful in treating diarrhea, hypertension, angina, platelet aggregation, cerebral spasm, premature labor, spontaneous abortion, dysmenorrhea, and migraine.

14 Claims, No Drawings

INDENYL HYDROXAMIC ACIDS AND HYDROXY UREAS AS INHIBITORS OF 5-LIPOXYGENASE

BACKGROUND OF THE INVENTION

The leukotrienes and their biological activities, especially their role in various disease states, have been extensively studied. Their properties are described in the book *Leukotrienes and Lipoxygenases*, Ed., J. Rokach, Elsevier, N.Y., 1989.

Inhibitors of the 5-lipoxygenase enzyme will prevent the biosynthesis of the various leukotrienes, and hence have a beneficial effect in those disease states in which the leukotrienes contribute to the disease.

Various derivatives of hydroxylamine have been described as inhibitors of the 5-lipoxygenase enzyme. Representative compounds are to be found in the following patent documents: EP 196,184, EP 279,263, WP 87/04152 and U.K. 2,191,194. None of the above-mentioned compounds contains an indene nucleus, a distinguishing feature of the present invention. U.S. Pat. Nos. 3,647,858 and 3,654,349 describe certain indene derivatives, which differ considerably from the present invention in that they are carboxylic acids rather than hydroxamic acid derivatives. Hydroxamic acids are distinguished from carboxylic acids by being about 4 $pK_A$ units weaker as acids. The $pK_A$ values of hydroxamic acids (8-9) are such that they are largely un-ionized at physiological pH, whereas carboxylic acids ($pK_A$ 4-5) are fully ionized. Other physical-chemical properties, such as chelation ability, are also notably different between the two classes of functional groups.

SUMMARY OF THE INVENTION

The present invention relates to compounds having activity as inhibitors of the 5-lipoxygenase enzyme, to methods for their preparation, and to methods and pharmaceutical formulations for using these compounds in mammals (especially humans).

Because of their activity as inhibitors of 5-lipoxygenase, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems for example, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

DETAILED DESCRIPTION OF THE INVENTION

The present invention provides novel compounds of the Formula I:

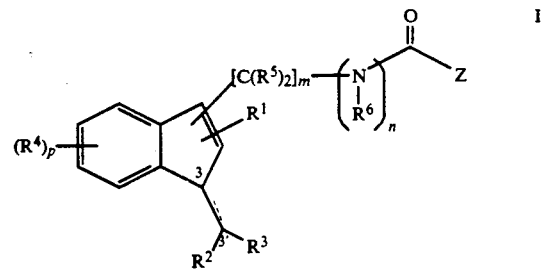

wherein:
$R^1$ and $R^5$ are independently:
  a) hydrogen;
  b) lower alkyl;
$R^2$ and $R^3$ are independently
  c) hydrogen;
  d) lower alkyl;
  e) phenyl substituted with c)-d) hereinabove or $R^7$; where $R^7$ is $-OR^8$, $-SR^9$, $-S(O)_2R^9$, $-CN$, $-CO_2R^8$, or halogen;
    wherein $R^8$ is hydrogen or $R^9$;
    $R^9$ is lower alkyl;
  f) heteroaryl substituted with c)-d) hereinabove or $R^7$;
  g) lower alkyl monosubstituted with e) to f) hereinabove;
R4 is hydrogen, lower alkyl, lower alkynyl, lower alkenyl, $-OR^8$, $-C(O)R^8$, $-NO_2$, $N(R^8)_2$, $-NR^8C(O)R^8$, $-R^{10}N(R^8_2)$, $SO_2N(R^8)_2$, $-SR^9$, $-R^{10}OH$, $-S(O)_2R^9$, $-CN$, $-CO_2R^8$, $-CON(R^8)_2$, halogen, cycloalkyl, $-R^{10}$—halogen, or cycloalkoxy; where $R^8$ and $R^9$ are defined hereinabove and $R^{10}$ is lower alkyl;
$R^6$ is hydrogen or OM;
M is hydrogen, a pharmaceutically acceptable cation or $-C(O)R^{11}$;
  where $R^{11}$ is lower alkyl, or phenyl substituted with hydrogen, lower alkyl or $R^7$;
m is 0 to 4;
n is 0 or 1;
p is 0 to 2;
Z is lower alkyl or $NR^{12}R^{13}$; where $R^{12}$ is OM or $R^{13}$; $R^{13}$ is hydrogen, lower alkyl or $R^{12}$ and $R^{13}$ are joined to form a heterocyclic ring of 3 to 6 carbon atoms and 1 or 2 heteroatoms selected from N, S or O, provided that $R^{12}$ is OM when $R^6$ is hydrogen or n is 0;
and the dotted line between positions 3 and 3' indicates an optional double bond.

Alkyl, alkenyl, and alkynl are intended to include linear and branched structures and combinations thereof.

As used herein, the term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

As used herein, the term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, and the like.

"Lower alkenyl" groups include those alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl and the like.

"Lower alkynyl" groups include those alkynyl groups of 2 to 7 carbon atoms. Examples of lower alkynyl groups include ethynyl, propargyl, 3-methyl-1-pentynyl, 2-heptynyl and the like.

The term "cycloalkyl" refers to a hydrocarbon containing one or more rings having from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo[4.4.0]decyl and the like.

The term "cycloalkoxy" refers to an oxygen attached to a hydrocarbon containing one or more rings having from 3 to 12 carbon atoms with the hydrocarbon having up to a total of 20 carbon atoms. Examples of cycloalkoxy groups are cyclopropoxy, cyclopentoxy, cyclododecyloxy, and the like.

The term "heteroaryl" which defines R2 and R3 refers to those monocyclic groups of 5 to 7 members containing only one heteroatom selected from N, S, or O in the ring. Examples include furanyl, pyridyl, thienyl and the like.

The term "suitably substituted hydroxylamine hydrochloride" refered to in the Methods section refers to hydroxylamine hydrochloride and lower alkyl hydroxylamine hydrochloride, the latter which includes methylhydroxylamine hydrochloride, ethylhydroxylamine hydrochloride and the like.

Halogen includes F, Cl, Br, and I.

It is intended that the definitions of any substituent (e.g., $R^4$, $R^5$, etc.) in a particular molecule be independent of its definitions elsewhere in the molecule. Thus, —$N(R^8)_2$ represents —NHH, —NHCH$_3$, etc.

It is intended that the point of attachment of the $R^1$ substituent may be either at the 1-position or the 2-position of the indene ring and that the $C(R^5)_2$ etc. substitutent is attached at the position not occupied by $R^1$. It is intended that the $R^4$ substituent(s) may occupy any of the nonfused positions of the 6-membered ring of the indene.

The heterocycles formed when $R^{12}$ and $R^{13}$ join through N include pyrrolidine, piperidine, morpholine, thiamorpholine, piperazine, and N-methylpiperazine.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or pharmaceutically acceptable salts thereof, and may also contain a pharmaceutically acceptable carrier and optionally other therapeutic ingredients.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Thus M includes the above cations.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

The ability of the compounds of Formula I to inhibit the 5-lipoxygenase enzyme makes them useful for inhibiting the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such asarthritis or inflammatory bowel disease, 4) pain, 5) skin conditions such as psoriasis and the like, 6) cardiovascular conditions such as angina, endotoxin shock, and the like and 7) renal insufficiency arising from ischaemia induced by immunological or chemical (cyclosporin) etiology and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient andeach cachet or capsule contains from about 2.5 to about 500 mg of the active ingredient.

The following are examples of representative pharmaceutical dosage forms for the compounds of Formula I:

| Injectable Suspension (I.M.) | mg/ml |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of | 1 ml |
| Tablet | mg/tablet |
| Compound of Formula I | 25 |
| Microcrystalline Cellulose | 415 |
| Providone | 14.0 |
| Pregelatinized Starch | 43.5 |
| Magnesium Stearate | 2.5 |
|  | 500 |
| Capsule | mg/capsule |
| Compound of Formula I | 25 |
| Lactose Powder | 573.5 |
| Magnesium Stearate | 1.5 |
|  | 600 |
| Aerosol canister | Per |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to aring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

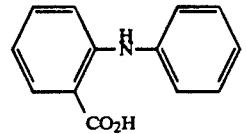

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

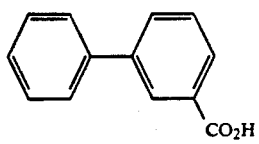

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

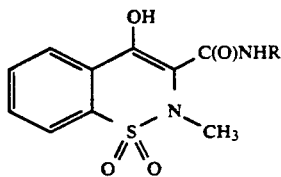

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (July 21, 1982) and 61,800 (June 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptorantagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxy-chromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

REPRESENTATIVE COMPOUNDS

Tables 1, 2 and 3 illustrate compounds representative of the present invention.

TABLE 1

Formula Ia: structure with $R^4$, $[CR_2^5]_m$-Y-C(=O)-Z, $R^1$, $R^2$, $R^3$ on an indene core.

| EX. | $[CR_2^5]_m$ | Y | Z | $R^1$ | $R^2$ | $R^3$ | $R^4$ |
|---|---|---|---|---|---|---|---|
| 1 | $CH_2$ | — | $N(OH)CH_3$ | $CH_3$ | H | $C_6H_4$-4-$SCH_3$ | F |
| 2 | $(CH_2)_2$ | NOH | $CH_3$ | $CH_3$ | H | $C_6H_4$-4-$SCH_3$ | F |
| 3 | $(CH_2)_2$ | NOH | $NH_2$ | $CH_3$ | H | $C_6H_4$-4-$SCH_3$ | F |
| 4 | $(CH_2)_2$ | NOH | $NHCH_3$ | $CH_3$ | H | $C_6H_4$-4-$SCH_3$ | F |
| 5 | $(CH_2)_2$ | NOH | $NH(CH_3)_3$ | $CH_3$ | H | $C_6H_4$-4-$SCH_3$ | F |
| 6 | $CH_2$ | NH | $N(OH)CH_3$ | $CH_3$ | H | $C_6H_4$-4-$SCH_3$ | F |
| 7 | $(CH_2)_2$ | NOH | $NH_2$ | $CH_3$ | H | $C_6H_4$-4-$S(O)CH_3$ | F |
| 8 | $(CH_2)_2$ | NOH | $NH_2$ | $CH_3$ | H | $C_6H_4$-4-$S(O)_2CH_3$ | F |
| 9 | $CH_2$ | NOH | $NH_2$ | $CH_3$ | H | $C_6H_4$-4-$SCH_3$ | F |
| 10 | $CHCH_3$ | NOH | $NH_2$ | $CH_3$ | H | $C_6H_4$-4-$SCH_3$ | F |
| 11 | $(CH_2)_3$ | NOH | $NH_2$ | $CH_3$ | H | $C_6H_4$-4-$SCH_3$ | F |
| 12 | $(CH_2)_4$ | NOH | $NH_2$ | $CH_3$ | H | $C_6H_4$-4-$SCH_3$ | F |
| 13 | $(CH_2)_2$ | NOH | $NH_2$ | H | $C_6H_4$-4-$SCH_3$ | H | H |
| 14 | $(CH_2)_2$ | NOH | $NH_2$ | H | $C_4H_3O$* | H | H |
| 15 | $(CH_2)_2$ | NOH | $NH_2$ | H | $C_4H_3S$** | H | H |

*2-FURYL
**2-THIENYL

TABLE 2

Formula Ib: structure with $CH_3$, $R^3$ substituents on indene with ethyl-N(OH)-C(=O)-$NH_2$ side chain.

| EX | $R^3$ |
|---|---|
| 16 | $C_6H_4$-4-$SCH_3$ |
| 17 | $C_6H_4$-4-$S(O)CH_3$ |
| 18 | $C_6H_4$-4-$S(O)_2CH_3$ |

TABLE 3

Structure with HO-N(C(=O)$NH_2$)-CH_2CH_2 side chain, $R^1$ and $CH_2R^3$ on indane.

| EX | $R^1$ | —$CH_2R^3$ |
|---|---|---|
| 19 | $CH_3$ | $CH_2C_6H_4$-4-$SCH_3$ |
| 20 | H | $CH_2CH_3$ |

ASSAYS FOR DETERMINING BIOLOGICAL ACTIVITY

Compounds of Formula I can be tested using the following assays to determine their ability to inhibit the 5-lipoxygenase enzyme.

DETERMINATION OF INHIBITION OF 5-LIPOXYGENASE

The activity of 5-lipoxygenase was measured from the conversion of [$^{14}$C]-arachidonic acid to 5-HETE and 5,12-diHETEs catalyzed by the 10,000×g supernatant fraction from rat PMN leukocytes, using the procedure of Riendeau and Leblanc (*Biochem. Biophys. Res. Commun.* 141, 534–540, 1986) with minor modifications. The incubation mixture contained 25 mM Na$^+$/K$^+$ phosphate buffer, pH 7.3, 1 mM ATP, 0.5 mM $CaCl_2$, 0.5 mM mercaptoethanol and an aliquot of the enzyme preparation in a final volume of 0.2 ml. The enzyme was pre-incubated with the inhibitor for 2 min at 37° C. before initiation of the reaction with the addition of 2 μl of [$^{14}$C]-arachidonic acid (25,000 DPM) in ethanol to obtain a final concentration of 10 μM. Inhibitors were added as 500-fold concentrated solutions in DMSO. After incubation for 10 min at 37° C., the reaction was stopped by adding 0.8 mL of diethyl ether/methanol/1M citric acid (30:4:1). The samples were centrifuged at 1,000×g for 5 min and the organic phases analyzed by TLC on Baker Si250F-PA or Whatman silica gel 60A LKGF plates using diethyl ether/petroleum ether/acetic acid (50:50:1) as solvent. The amount of radioactivity migrating at the positions of arachidonic acid, 5-HETE and 5,12-diHETEs was determined using a Berthold TLC analyzer LB 2842. The activity of 5-lipoxygenase was calculated from the percentage of conversion of arachidonic acid to 5-HETE and 5,12-diHETEs after the 10 min incubation.

RAT PERITONEAL POLYMORPHONUCLEAR (PMN) LEUKOCYTE ASSAY

Rats under ether anesthesia are injected (i.p.) with 8 mL of a suspension of sodium caseinate (6 grams in ca. 50 mL water). After 15-24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/mL. A 500 μL aliquot of PMN suspension and test compound are preincubated for 2 minutes at 37°, followed by the addition of 10 μM A-23187. The suspension is stirred for an additional 4 minutes then bioassayed for $LTB_4$ content by adding an aliquot to a second 500 μL portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

HUMAN POLYMORPHONUCLEAR (PMN) LEUKOCYTE $LTB_4$ ASSAY

A. Preparation of Human PMN. Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum.[1] Contaminating erythrocytes were removed by lysis following exposure to ammonium chloride (0.16M) in Tris buffer (pH 7.65), and the PMNs resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4. Viability was assessed by Trypan blue exclusion and was typically greater than 98%.
(1) Boyum, A. Scand. J. Clin. Lab. Invest., 21: (Supp 97), 77 (1968).

B. Generation and Radioimmunoassay of $LTB_4$. PMNs (0.5 mL; $2.5 \times 10^5$ cells) were placed in plastic tubes and incubated (37° C., 2 min) with test compounds at the desired concentration or vehicle (DMSO, final concentration 0.2%) as control. The synthesis of $LTB_4$ was initiated by the addition of calcium ionophore A23187 (final concentration 10 μM) or vehicle in control samples and allowed to proceed for 5 minutes at 37° C. The reactions were then terminated by the addition of cold methanol (0.25 mL) and samples of the entire PMN reaction mixture were removed for radioimmunoassay of $LTB_4$.

Samples (50 μL) of authentic $LTB_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter $[^3H]$-$LTB_4$ (10 nCi in 100 μL RIA buffer) and $LTB_4$-antiserum (100 μL of a 1:3000 dilution in RIA buffer) were added and the tubes vortexed. Reactants were allowed to equilibrate by incubation overnight at 4° C. To separate antibody-bound from free $LTB_4$, aliquots (50 μL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatants containing antibody-bound $LTB_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al.[2] The amount of $LTB_4$ produced in test and control (approx. 20 ng/$10^6$ cells) samples were calculated. Inhibitory dose-response curves were constructed using a four-parameter algorithm and from these the $IC_{50}$ values were determined.
(2) Rokach, J.; Hayes, E. C.; Girard, Y,; Lombardo, D. L.; Maycock, A. L.; Rosenthal, A. S.; Young, R. N.; Zamboni, R.; Zweerink, H. J. Prostaglandins Leukotrienes and Medicine, 13:21 (1984).

ASTHMATIC RAT ASSAY

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 Mgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Compounds of the present invention can be prepared according to the following methods. Temperatures are in degree Celsius.

It will be apparent to one skilled in the art that the various functional groups ($R^1$, $R^2$, $R^6$ etc.) must be chosen so as to be compatible with the chemistry being carried out. Such compatibility can often be achieved by protecting groups, or by specific variations in the sequence of the reactions.

When $R^4$ or $R^7$ is S—$R^9$, the corresponding sulfoxides and sulfones can be prepared by oxidation of the sulfides with one or two equivalents of an oxidizing agent such as m-chloroperbenzoic acid or monoperoxyphthalic acid or oxone (Trost, J. Org. Chem., 1988, pg. 532).

Many of the following methods involve a basic hydrolysis of an ester function to obtain the corresponding carboxylic acid. In all cases, the free acid is obtained by acidification of the reaction mixture with a suitable acid such as hydrochloric, sulfuric, acetic, trifluoracetic acid, etc.

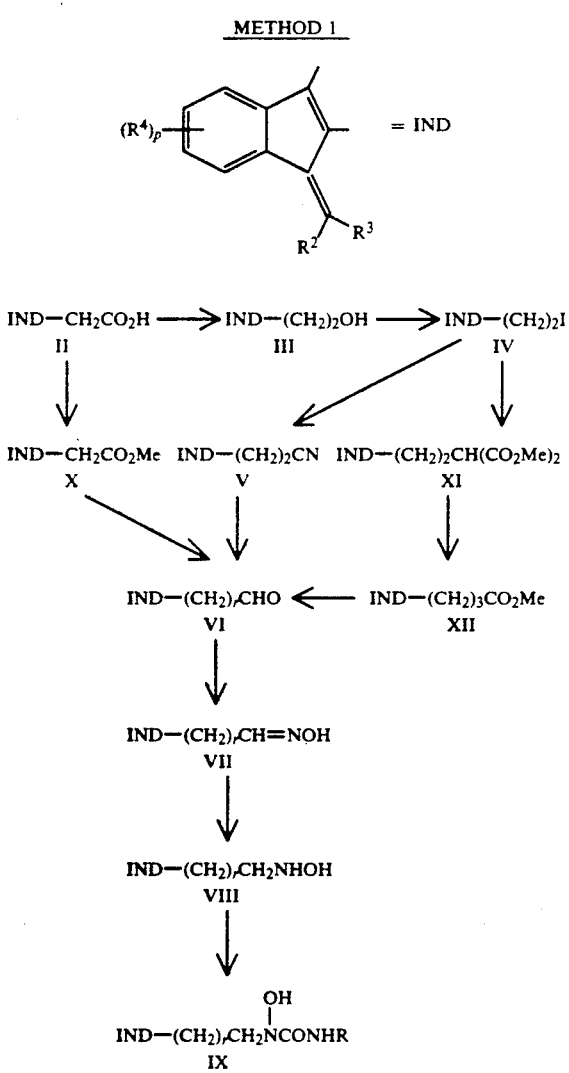

METHOD 1

Intermediate III is prepared by reduction of the indene carboxylic acid II with a reducing agent, such as borane or lithium aluminum hydride, in a suitable organic solvent, such as tetrahydrofuran (THF). The hydroxyethylindene III is converted to the iodoethylindene IV by treatment with an iodine source, such as tetrabutylammonium iodide, in the presence of a hydroxyl-activating agent, such as trifluoromethane sulfonic anhydride, in a suitable organic solvent, such as methylene chloride. The intermediate IV so obtained is converted to the cyanoethylindene V by treatment with a cyanide source, such as potassium cyanide or tetrabutylammonium cyanide, in a suitable organic solvent, such as acetonitrile or dimethylformamide (DMF). The nitrile V is then reduced to the aldehyde VI (r=2) by treatment with a reducing agent, such as diisobutyl aluminum hydride, in a suitable organic solvent such as toluene.

The aldehyde VI so obtained is treated with hydroxylamine hydrochloride in the presence of an organic nitrogen base, such as triethylamine, in a suitable organic solvent, such as ethanol, to provide the oxime VII (r=2). The oxime VII is converted to the hydroxaminoethylindene VIII (r=2) by reducing it with a suitable reducing agent, such as pyridine-borane complex, in the presence of a proton source, such as aqueous hydrochloric acid, in a suitable water-miscible organic solvent, such as ethanol. The hydroxamine VIII so obtained is treated with trimethylsilyl isocyanate in a suitable organic solvent, such as THF, followed by treatment with water to provide a compound IX (r=2, R=H) of the present invention.

Alternatively, the indene carboxylic acid II may be esterified by treating it with thionyl chloride with methanol to provide the ester X. This ester X is converted to the aldehyde VI (r=1) by treatment with a suitable reducing agent, such as diisobutyl aluminum hydride, in a suitable organic solvent, such as toluene. The aldehyde VI so obtained may undergo the sequence of reactions described above to provide a compound IX (r=1, R=H) of the present invention.

Alternatively, the iodoethylindene IV described above is treated with the sodium salt of dimethyl malonate in a suitable organic solvent, such as DMF, to provide the malonate XI. The dimethyl malonate XI is converted to the methyl ester XII by treatment with lithium chloride and water in a suitable water miscible organic solvent, such as dimethyl sulfoxide (DMSO). This ester XII is converted to the aldehyde VI (r=3) as described for ester X. The aldehyde so obtained is converted to a compound IX (r=3, R=H) of the present invention by the sequence of reactions described above.

Reacting compound VIII (r=1) with methyl isocyanate or with t-butyl isocyanate in THF provides compound IX (r=1, R=methyl or t-butyl) of the present invention.

METHOD 2

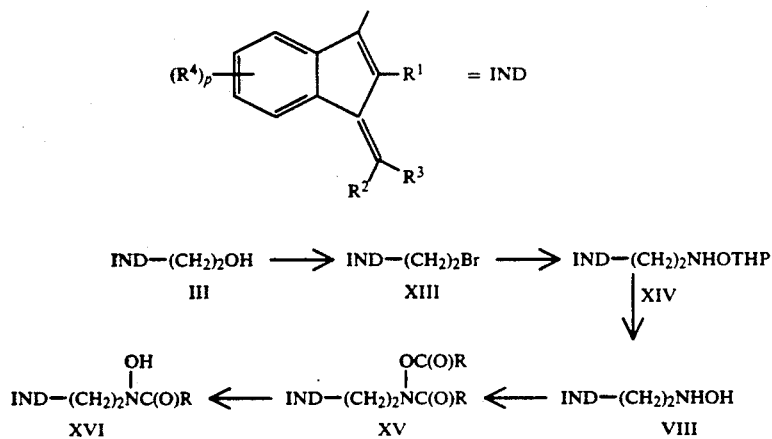

IND—(CH₂)₂OH  →  IND—(CH₂)₂Br  →  IND—(CH₂)₂NHOTHP
　　III　　　　　　　　XIII　　　　　　　　　↓ XIV

OH　　　　　　　　　　OC(O)R
IND—(CH₂)₂NC(O)R  ←  IND—(CH₂)₂NC(O)R  ←  IND—(CH₂)₂NHOH
　　　XVI　　　　　　　　　XV　　　　　　　　　　VIII

METHOD 2

Intermediate XIII is prepared by treatment of the hydroxyethylindene III with carbon tetrabromide and 1,2-bis(diphenylphosphino)ethane in a suitable organic solvent, such as methylene chloride. The bromoethylindene XIII so obtained is treated with a suitably protected hydroxylamine such as O-(tetrahydropyran-2-yl)hydroxylamine and potassium iodide in a suitable organic solvent, such as DMF or acetone, to provide intermediate XIV. The intermediate XIV is deprotected by treatment with an organic acid such as camphorsulfonic acid in a suitable organic solvent such as methanol to provide the hydroxylaminoethylindene VIII. The intermediate VIII is converted to the acyloxyacylamide XV by treating VIII with a suitable acylating agent, such as an acid chloride (RCOCl) or an acid anhydride ((RCO)₂O), and a suitable organic base, such as pyridine, in a suitable organic solvent, such as methylene chloride. The intermediate XV is converted to a compound XVI of the present invention by treatment of XV with a suitable weak base, such as potassium carbonate, in a suitable organic solvent, such as methanol. R is Z in the Formula I compounds.

METHOD 3

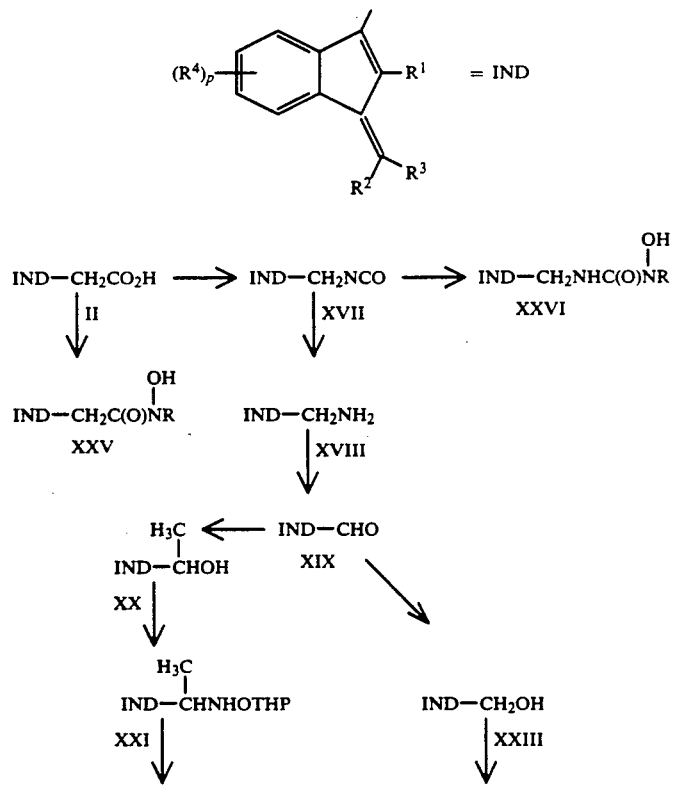

METHOD 3

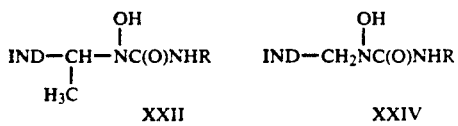

METHOD 3

The indene carboxylic acid II is treated with oxalyl chloride and DMF in a suitable organic solvent such as methylene chloride and the resulting acid chloride is treated with an azide source, such as trimethylsilyl azide or sodium azide, in a suitable organic solvent, such as carbon tetrachloride or acetonitrile, to provide the isocyanate XVII. The isocyanate thus obtained is hydrolyzed to the aminomethylindene XVIII, as the hydrochloride salt, with acetic acid and aqueous hydrochloric acid. The free amine XVIII is obtained by neutralizing the hydrochloride salt with an alkali base, such as sodium hydroxide, in a mixture of water and a suitable organic solvent, such as ethyl acetate (EtOAc). The aminomethylindene XVIII is converted to the aldehyde XIX by first treating the amine with a suitable chlorinating agent, such as t-butyl hypochlorite, in a suitable organic solvent, such as diethyl ether or tetrahydrofuran, followed by a suitable organoalkali base, such as potassium t-butoxide, in a suitable organic solvent, such as ethanol.

The aldehyde XIX thus obtained is reductively alkylated to the hydroxyethylindene XX by treating compound XIX with a suitable methylating agent, such as methyl lithium, in a suitable organic solvent, such as THF and ether, followed by contacting the intermediate with a suitable proton source, such as ammonium chloride in water. The alcohol XX thus obtained is converted to intermediate XXI by treating it with O-(tetrahydropyran-2-yl)hydroxylamine and a suitable organic acid, such as trifluoracetic acid, in a suitable organic solvent, such as methylene chloride. The intermediate XXI is deprotected as described in Method 2 for intermediate XIV and is then converted to a compound XXII of the present invention by derivatizing as described in Method 1 for hydroxamine VIII.

Alternately, the aldehyde XIX is reduced by contacting the aldehyde with a suitable reducing agent, such as a combination of cerous chloride and sodium borohydride, in a suitable organic solvent, such as ethanol and THF, to provide the hydroxymethylindene XXIII. The intermediate XXIII is then converted to a compound XXIV of the present invention by the same sequence of reactions as described in Method 2 to provide intermediate VIII followed by the reactions as described in Method 1 to convert intermediate VIII to compound IX.

Alternately, the indene carboxylic acid II is treated with oxalyl chloride and DMF in a suitable organic solvent, such as methylene chloride, and this solution is added to a mixture of a suitable hydroxylamine hydrochloride, such as N-methyl hydroxylamine hydrochloride, and a suitable organic nitrogen base, such as triethylamine, in a suitable organic solvent, such as THF, to provide a compound XXV (R=Me) of the present invention.

Alternately, the indene isocyanate XVII is treated with a suitable hydroxylamine hydrochloride, such as N-methylhydroxylamine hydrochloride, and a suitable organic nitrogen base, such as triethylamine, in a suitable organic solvent, such as THF, to provide XXVI (R=Me) of the present invention.

METHOD 4

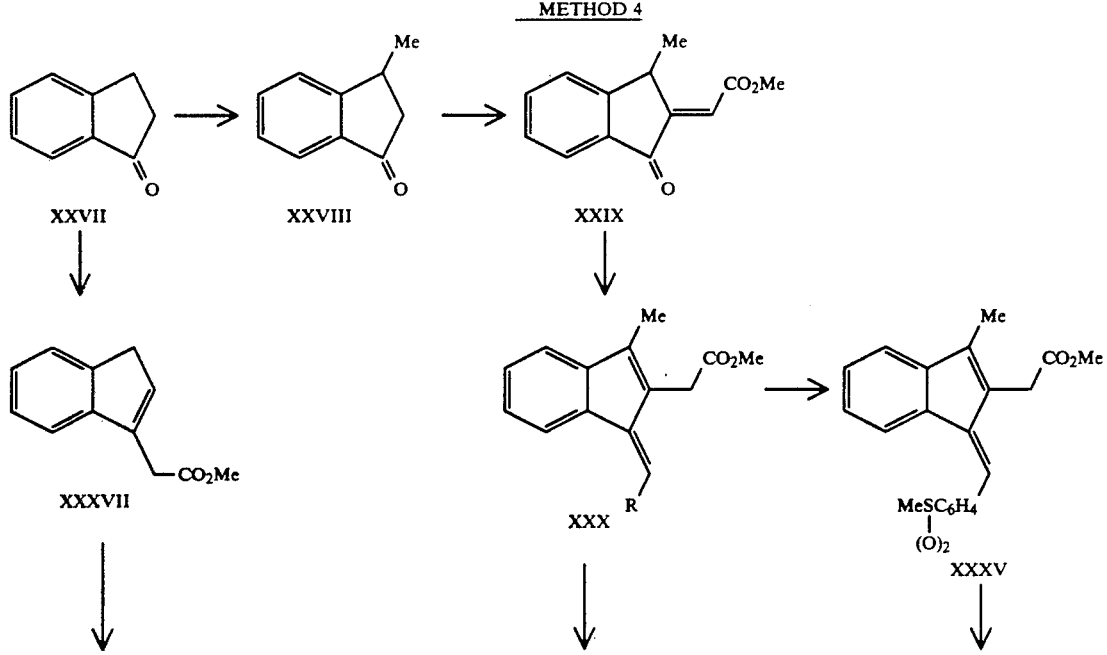

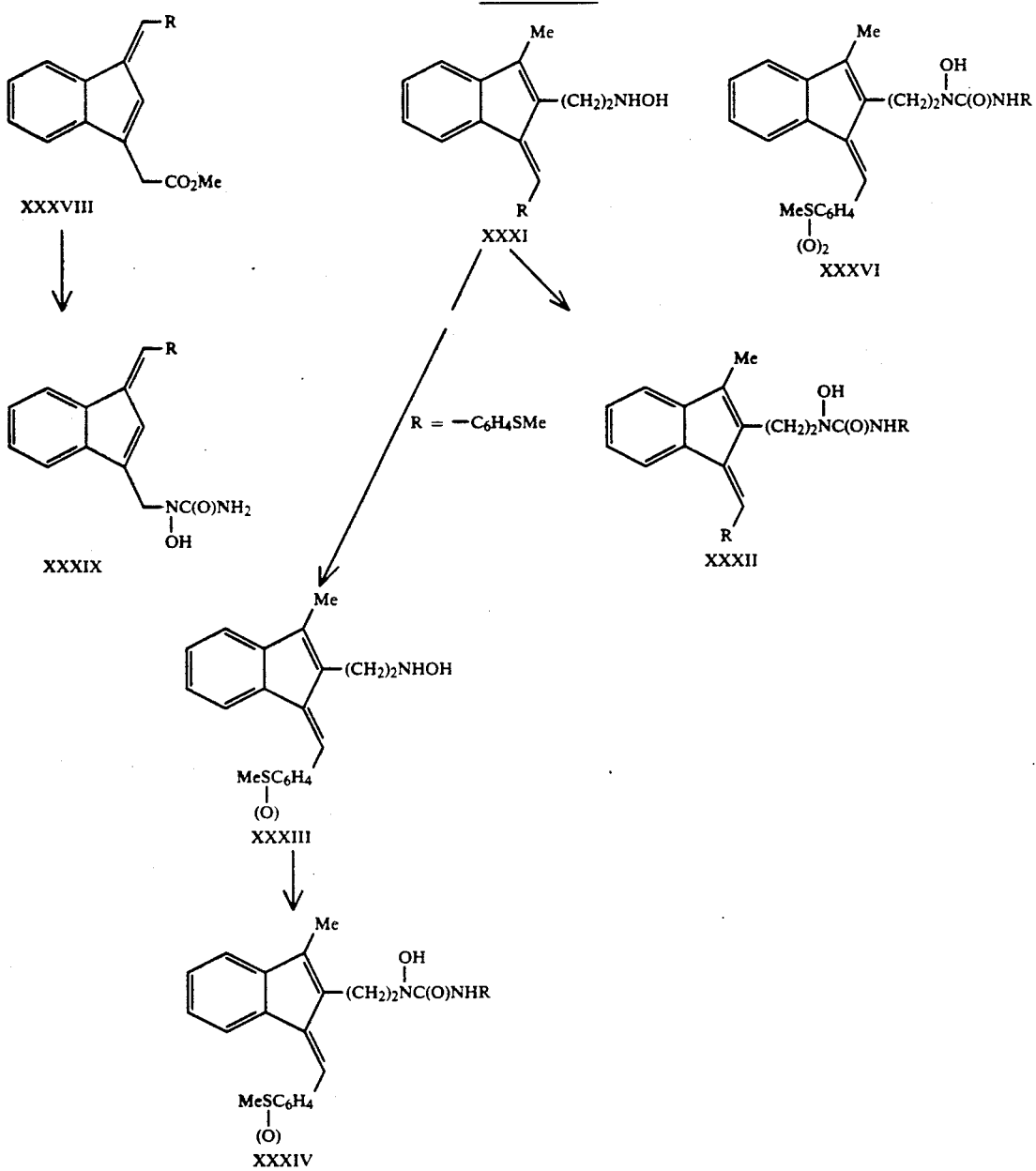

-continued
METHOD 4

METHOD 4

Intermediate XXVIII is treated with glyoxylic acid hydrate and a suitable strong acid, such as sulfuric acid, in a suitable organic solvent, such as dioxane. The product from this reaction is treated with methanol and thionyl chloride to provide the methyl ester XXIX. The intermediate XXIX is treated with a suitably substituted methylmagnesium halide, such as 4-methylthiobenzylmagnesium bromide, in a suitable organic solvent, such as ether, to provide the intermediate XXX.

Intermediate XXX is reduced by contacting it with a suitable reducing agent, such as diisobutyl aluminum hydride, in a suitable organic solvent, such as THF and toluene. The alcohol obtained this way is oxidized with a suitable oxidizing agent, such as a chromium trioxide/pyridine mixture, in a suitable organic solvent, such as methylene chloride. The aldehyde obtained in this way undergoes the procedure described in Method 1 for aldehyde VI to provide the hydroxamine XXXI. The intermediate XXXI is then treated as described in Method 1 for intermediate VIII to provide a compound XXXII of the present invention.

When the R group in intermediate XXXI is a methylthiophenyl group oxidation of XXXI with approximately one molar equivalent of a suitable oxidizing agent, such as m-chloroperoxy benzoic acid, in a suitable organic solvent, such as methylene chloride provides the sulfoxide XXXIII. The intermediate XXXIII is then treated as described in Method 1 for intermediate VIII to provide a compound XXXIV of the present invention.

When the R group in intermediate XXX is a methylthiophenyl group oxidation of intermediate XXX with greater than 2 molar equivalents of a suitable oxidizing agent, such as m-chloroperoxy benzoic acid, in a suitable organic solvent, such as methylene chloride, provides the sulfone XXXV. The intermediate XXXV is then treated as described in Method 1 for intermediate X to provide a compound XXXVI of the present invention.

Intermediate XXVII is treated with zinc, methylbromoacetate and iodine in a suitable organic solvent, such as ethyl ether, and after the mixture is refluxed for a sufficient time, such as 3 hours, the mixture is treated with a suitable strong acid, such as aqueous hydrochloric acid, to decompose the zinc complex. The product from this reaction is treated with formic acid which provides the ester intermediate XXXVII. The ester XXXVII is treated with a suitable strong base, such as lithium diisopropyl amide, in a suitable organic solvent, such as THF, then a suitably substituted aldehyde, such as 4-methylthiobenzaldehyde, 2-furaldehyde or 2-thiophene carboxaldehyde, is added. The compound so produced is treated with a suitable strong base, such as Triton B, in a suitable organic solvent, such as methanol, which provides, after acidification with a suitable aqueous acid, such as aqueous hydrochloric acid, and subsequent treatment with diazomethane, provides the intermediate XXXVIII. The intermediate XXXVIII is then treated as described in Method 1 for intermediate X which provides a compound XXXIX of the present invention.

METHOD 5

Intermediate XL is treated with a suitable strong base, such as LDA, in a suitable organic solvent, such as THF and the resulting solution was treated with a suitably substituted alkyl halide (R—hal), such as 4-methylthiobenzyl chloride, providing the intermediate XLI. Intermediate XLI is treated as described in Method 4 for intermediate XXV to provide intermediate XLII which in turn is treated as described in Method 1 for intermediate VIII to provide a compound XLIII of the present invention.

Intermediate XXXVII, described in Method 4, is treated as described above for intermediate XL to provide the ester intermediate XLIV. Intermediate XLIV is treated as described in Method 1 for intermediate VIII to provide a compound XLV of the present invention. R is —CH$_2$—phenyl, as described under definition e) of R$^2$ and R$^3$, or alkyl.

EXAMPLES

The invention is further defined by reference to the following examples, which are intended to be illustrative and not limiting. All temperatures are in degrees Celsius.

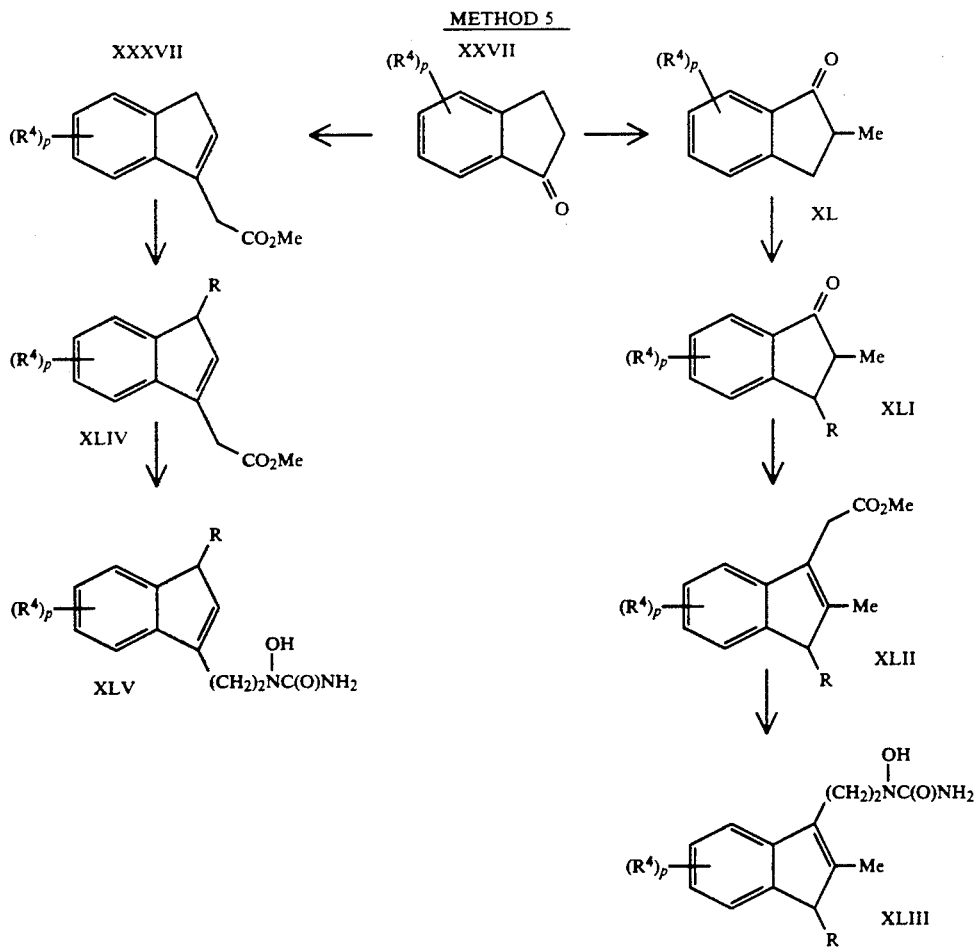

EXAMPLE 1

(Z)-N-Hydroxy-N-methyl-5-fluoro-2-methyl-1-(4-methylthiobenzylidene)inden-3-ylacetamide To a suspension of (Z)-5-fluoro-2-methyl-1-(4-methylthiobenzylidene) inden-3-ylacetic acid (U.S. Pat. No. 3,647,858; U.S. Pat. No. 3,654,349; J.O.C. Vol 42, 1914–1919 (1977) (130 mg, 0.38 mmol) in methylene chloride (3 mL) at room temperature there was added oxalyl chloride (96.5 mg, 0.76 mmol) and one drop of N,N-dimethylformamide (DMF). When gassing had subsided another drop of DMF was added and stirring was continued for 30 minutes. This solution was added, at 0° C., to a mixture of N-methyl hydroxylamine hydrochloride (125 mg, 1.5 mmol) and triethylamine (253 mg, 2.5 mmol) in tetrahydrofuran (THF) (5 mL). After 30 minutes at 0° C., the mixture was diluted with water and ethyl acetate and acidified with 1N aqueous HCl. The crude product from the organic extract was crystallized from a mixture of ethyl acetate and hexane to afford the title product as yellow-orange crystals, mp: slow decomp. from 118° C.

EXAMPLE 2

(Z)-N-{2-[5Fluoro-2-methyl-1-(4-methylthio benzylidene)inden-3-yl]ethyl}-N-hydroxyacetamide Step 1: (Z)-N-Acetoxy-{N-2-[5-fluoro-2-methyl-1-(4-methylthiobenzylidene)inden-3-yl]ethyl}acetamide To a suspension of (Z)-3-(2-hydroxaminoethyl)-5-fluoro-2-methyl-1-(4-methylthiobenzylidene) indene from Example 3, Method A, Step 4 and Method B, Step 4 (220 mg, 0.645 mmol) in methylene chloride (8 mL) there was added pyridine (253 mg, 3.2 mmol) and acetyl chloride (151 mg, 1.93 mmol). The mixture was stirred at room temperature for 1 hour. Then it was diluted with methylene chloride, washed successively with water, 1N aqueous HCl, water, saturated aqueous NaHCO$_3$ and water. After drying over Na$_2$SO$_4$, the solvent was evaporated away and the crude title compound used as such for the next step.

Step 2: (Z)-N-{2-[5-fluoro-2-methyl-1-(4-methylthiobenzylidene)inden-3-yl]ethyl}-N-hydroxyacetamide The crude diacetylated product from Step 1 was suspended in methanol (10 mL), potassium carbonate (51 mg, 0.368 mmol) was added and the mixture stirred at room temperature for 1 hour. The methanol was evaporated and the residue partitioned between ethyl acetate and water. The residue from evaporation of the organic fraction was triturated with ether and filtered to afford the title product as a yellow solid, mp: 149°–151° C., dec.

EXAMPLE 3

(Z)-N-{2-[5-Fluoro-2-methyl-1-(4-methylthiobenzylidene)inden-3-yl]ethyl}-N-hydroxyurea

METHOD A

Step 1: Methyl (Z)-5-fluoro-2-methyl-1-(4-methylthiobenzylidene)inden-3-ylacetate To a suspension of (Z)-5-fluoro-2-methyl-1-(4-methylthiobenzylidene)inden-3-ylacetic acid (51 g, 0.15 mol) in methanol (600 mL) at 0° C. there was slowly added thionyl chloride (26.8 g, 0.225 mol). The mixture was then stirred at room temperature for 2 hours and filtered to afford the title compound as a yellow solid, mp 73°–75° C.

Step 2: (Z)-5-Fluoro-2-methyl-1-(4-methylthiobenzylidene)inden-3-ylacetaldehyde

To a solution of the ester from Step 1 (3.39 g, 9.57 mmol) in toluene (75 mL) at −70° C., there was slowly added diisobutyl aluminum hydride (1M) in toluene (12 mL, 12 mmol) and the resulting mixture stirred at −70° C. for 45 minutes. Methanol (10 mL) was added slowly at −70° C., then the mixture was warmed to room temperature and water (100 mL) and 1N aqueous HCl (50 mL) were added. The mixture was shaken and the organic layer collected; the aqueous fraction was extracted with ether and the combined organic fractions washed 3 times with water, dried over MgSO$_4$ and evaporated down to a thick oil. The crude title compound was used as such in the next step.

Step 3: (Z)-5-Fluoro-2-methyl-1-(4-methylthiobenzylidene)-3-(2-hydroximinoethyl)indene A mixture of the acetaldehyde derivative from Step 2 (3.3 g, 10.18 mmol), hydroxylamine hydrochloride (1.42 g, 20.4 mmol), ethanol (25 mL) and triethylamine (2.06 g, 20.4 mmol) was stirred at room temperature for 30 minutes. The solvent was evaporated away and the residue was partitioned between ethyl acetate and water. The crude product from the organic phase was purified by column chromatography on silica gel using a 1:2 mixture of ethyl acetate:hexane as eluent. The title compound was obtained as a yellow solid, mp: 146°–150° C.

Step 4 (Z)-5-fluoro-3-(2-Hydroxaminoethyl)-2-methyl-1-(4-methylthiobenzylidene)indene To a suspension of the oxime from Step 3 (2.0 g, 5.9 mmol) in ethanol (35 mL) at 0° C. there was added pyridine-borane (1.1 g, 11.8 mmol) and 12N aqueous HCl (1.48 mL, 17.75 mmol). The mixture was stirred at 0° C. for 1 hour, then warmed to room temperature. Most of the ethanol was evaporated, the residue diluted with water and ethyl acetate (the product as hydrochloride salt remains in the organic phase) and basified with 1N aqueous NaOH. The product obtained from the organic phase was triturated with hexane and filtered to afford the title compound as a yellow solid, mp: 126° C. dec.

Analysis: Calc'd for C$_{20}$H$_{20}$FNOS: C, 70.35; H, 5.90; N, 4.10; S, 9.39; F, 5.56. Found: C, 70.51; H, 6.27; N, 4.15; S, 9.40; F, 5.62.

Step 5: (Z)-N-{2-[5-Fluoro-2-methyl-1-(4-methylthiobenzylidene)inden-3-yl]ethyl}-N-hydroxyurea To a solution of the hydroxylamine intermediate from Step 4 (1.62 g, 4.7 mmol) in THF (15 mL) there was added 85% trimethylsilyl isocyanate (954 mg, 7.25 mmol). The mixture was stirred at room temperature for 30 minutes. Water (10 mL) was added and stirring was continued for a further 10 minutes. Ethyl acetate was then added, the organic layer was decanted, washed with brine, dried over MgSO$_4$ and evaporated to dryness. The residue was triturated with ether and filtered to afford the pure title product as a yellow solid, mp: 149° C. dec.

METHOD B

Step 1: (Z)-5-Fluoro-3-(2-hydroxyethyl)-2-methyl-1-(4-methylthiobenzylidene)indene To a solution of (Z)-5-fluoro-2-methyl-1-(4-methylthiobenzylidene)inden-3-ylacetic acid, (1.70 g, 5 mmol) in THF (25 mL) at 0° C. and under nitrogen atmosphere, there was added a solution of borane (1M) in THF (5.5 mL, 5.5 mmol) and the mixture stirred in the cold for 30 minutes, then at room temperature for 2 hours. More borane was added (2.5 mL) and stirring was continued for 1 hour. Water was added slowly (20 mL), the THF was evaporated away and the residue partitioned between water and ethyl acetate. The crude product from the organic phase was purified by chromatography on silica gel using a 1:2 mixture of ethyl acetate-hexane as eluent to afford the desired product (1.25 g) as a yellow oil which solidified on standing. This was triturated with hexane and filtered to yield the title compound as a yellow solid, mp 101°-103° C.

Step 2: (Z)-3-(2-Bromoethyl)-5-fluoro-2-methyl-1-(4-methylthiobenzylidene)indene To a solution of the alcohol from Step 1 (4.8 g, 14.7 mmol) and carbon tetrabromide (6.34 g, 19.1 mmol) in methylene chloride (100 mL) at 0° C. there was added, in portions, 1,2-bis(diphenylphosphino)ethane (6.34 g, 17.3 mmol). The mixture was stirred at 0° C. for 1 hour, and the solvent was evaporated. The residue was stirred in a mixture of ethyl acetate and water (150 mL each) for 30 minutes. After filtration, the organic portion of the filtrate was evaporated down and the crude product purified by column chromatography on silica gel using 10% ethyl acetate in hexane as eluent to afford pure title compound as a yellow oil which solidified on standing.

Step 3: (Z)-5-Fluoro-2-methyl-1-(4-methylthiobenzylidene)-3-[2-((tetrahydropyran-2-yl) hydroxamino)ethyl]indene A mixture of the bromide derivative from Step 2 (4.86 g, 12.5 mmol), 0-(tetrahydropyran-2-yl) hydroxylamine (4.39 g, 37.5 mmol) and potassium iodide (2.08 g, 12.5 mmol) in DMF (50 mL) was heated at 80° C. for 9 hours. After standing at room temperature overnight, the mixture was diluted with ether, washed four times with water, dried over MgSO$_4$ and evaporated to dryness. The crude product was purified by column chromatography on silica gel using a 60:40 mixture of hexane-ethyl acetate as eluent yielding pure title compound as a thick oil which was used in the next step.

Step 4: (Z)-5-fluoro-3-(2-Hydroxaminoethyl)-2-methyl-1-(4-methylthiobenzylidene)indene A mixture of the indene intermediate from Step 3 (1 g, 2.35 mmol) and (1R)-(−)-10-camphorsulfonic acid (546 mg, 2.35 mmol) in methanol (30 mL) was refluxed for 3 hours. The methanol was evaporated, the residue dissolved in ethyl acetate and the solution washed successively with water, twice with saturated aqueous sodium bicarbonate, and with water. After drying over Na$_2$SO$_4$, the residue obtained on evaporation of the solvent was triturated with ether and filtered to obtain the title compound as a yellow solid, mp: dec 126° C. which was identical to the product obtained in Method A, Step 4.

Conversion of this intermediate to the title compound was performed following the procedure of Method A, Step 5.

EXAMPLE 4

(Z)-N-{2-[5-Fluoro-2-methyl-1-(4-methylthiobenzylidene)inden-3-yl]ethyl}-N-hydroxy-N'-methylurea To a solution of (Z)-3-(2-hydroxaminoethyl)-5-fluoro-2-methyl-1-(4-methylthiobenzylidene)indene from Example 3, Method A, Step 4 (34 mg, 0.1 mmol) in THF (0.5 mL), there was added methyl isocyanate (11.4 mg, 0.2 mmol) and the mixture stirred at room temperature for 1 hour. The solvent was evaporated and the residue triturated with hexane and filtered to afford the title product as a yellow-orange solid, mp: dec 138° C.

EXAMPLE 5

(Z)-N-{2-[5-Fluoro-2-methyl-1-(4-methylthiobenzylidene)inden-3-yl]ethyl}-N-hydroxy-N'-t-butyl urea Following the procedure of Example 4, but substituting t-butyl isocyanate for methyl isocyanate, the title product was obtained in 75% yield as a yellow solid, mp: dec 134° C.

EXAMPLE 6

(Z)-N-[5-Fluoro-2-methyl-1-(4-methylthiobenzylidene)inden-3-ylmethyl]-N'-hydroxy-N'-methyl urea Step 1: (Z)-5-Fluoro-2-methyl-1-(4-methylthiobenzylidene)inden-3-ylmethyl isocyanate To a suspension of (Z)-5-fluoro-2-methyl-1-(4-methylthiobenzylidene)inden-3-ylacetic acid (5.0 g, 14.7 mmol) in methylene chloride (50 mL) at room temperature there was added oxalyl chloride (2.8 g, 22 mmol) and DMF (2 drops) and the mixture stirred for 1 hour; the solution was evaporated and the crude acid chloride flushed twice with carbon tetrachloride (20 mL) then suspended in carbon tetrachloride (25 mL) and trimethylsilyl azide (2.53 g, 22 mmol) was added. The mixture was stirred at room temperature for 15 minutes, then gently heated on a steam bath as nitrogen was evolved. The heating was continued until gas evolution ceased, then the mixture was evaporated to afford the crude title compound as an oil which was used as such in the next step.

Step 2: (Z)-N-[5-Fluoro-2-methyl-1-(4-methylthiobenzylidene)inden-3-ylmethyl]-N'-hydroxy-N'-methyl urea To a suspension of N-methyl hydroxylamine hydrochloride (9.82 g, 117.6 mmol) in THF (150 mL) at room temperature there was added triethylamine (16.3 mL, 117.6 mmol) and the mixture stirred for 10 minutes. There was added, over 15 minutes, a solution of the isocyanate from Step 1 in THF (100 mL). After 2 hours of stirring at room temperature, the THF was evaporated and the residue, on trituration with water, afforded a yellow solid which was filtered. This solid was stirred in ether (150 mL) and filtered again. This crude material was chromatographed on silica gel eluting with 5% ethanol in methylene chloride. The more polar component of the mixture was stirred with methylene chloride (50 mL) for 2 hours and filtered and the solid crystallized from ethyl acetate to afford the pure title product as yellow crystals, mp 190°-192° C. dec.

Analysis: Calc'd for $C_{21}H_{21}FN_2O_2S$: C, 65.60; H, 5.51; N, 7.29; S, 8.34; F, 4.94. Found: C, 65.88; H, 5.43; N, 7.58; S, 8.27; F, 4.99.

EXAMPLE 7

(Z)-N-{2-[5-Fluoro-2-methyl-1-(4-methylsulfinylbenzylidene)inden-3-yl]ethyl}-N-hydroxy urea Following the procedure of Example 3, Method A, but substituting (Z)-5-fluoro-2-methyl-1-(4-methylsulfinylbenzylidene)inden-3-ylacetic acid (Sulindac) (U.S. Pat. No. 3,647,858; U.S. Pat. No. 3,654,349; J.O.C. Vol 42, 1914–1919 (1977)) for (Z)-5-fluoro-2-methyl-1-(4-methylthiobenzylidene) inden-3-ylacetic acid as starting material, the title compound was obtained as a yellow solid, mp: 132° C. dec.

EXAMPLE 8

(Z)-N-{-2-[5-Fluoro-2-methyl-1-(4-methylsulfonylbenzylidene)inden-3-yl]ethyl}-N-hydroxy urea Step 1: Methyl (Z)-5-fluoro-2-methyl-1-(4-methylsulfonylbenzylidene)inden-3-ylacetate To a solution of methyl (Z)-5-fluoro-2-methyl-1-(4-methylsulfinyl benzylidene)inden-3-ylacetate from Example 7 (3.7 g, 10 mmol) in methylene chloride (100 mL) there was added 85% m-chloroperoxy benzoic acid (2.54 g, 12.5 mmol) and the mixture was stirred at room temperature for 1 hour. There was added more methylene chloride (100 mL) then calcium hydroxide (5.5 g) and after 10 minutes, the suspension was filtered. The residue obtained by evaporation of the filtrate was stirred with ether (100 mL) at room temperature for 5 hours, then filtered to afford the title compound as a fluffy yellow solid, mp 162°-164° C.

Step 2: (Z)-5-Fluoro-3-(2-hydroxyethyl)-2-methyl-1-(4-methylsulfonylbenzylidene)indene To a solution of the ester from Step 1 (2.7 g, 7 mmol) in THF (20 mL) at 0° C. there was added diisobutyl aluminum hydride (1M) in toluene (17 mL, 17 mmol) and the mixture was stirred at 0° C. for 1 hour, then quenched with methanol (10 mL). Ethyl acetate and 1N aqueous HCl were added and after collection of the organic phase the aqueous phase was extracted once more with ethyl acetate. The combined organic extracts, after washing with water three times and drying over Na$_2$SO$_4$, afforded on evaporation a yellow residue which was triturated with ether to afford the title compound as a yellow solid, mp: 102°-104° C.

Step3: (Z)-N-{-2-[5-Fluoro-2-methyl-1-(4-methylsulfonybenzylidene)inden-3-yl]ethyl}-N-hydroxy urea Following the procedure of Example 3, Method B, Steps 2-5, but substituting the alcohol intermediate from Step 2 for (Z)-5-fluoro-3-(2-hydroxyethyl)-2-methyl-1-(4-methylthiobenzylidene)indene as starting material, the title compound was obtained as a yellow solid, mp: 187° C.

EXAMPLE 9

(Z)-N-[5-Fluoro-2-methyl-1-(4-methylthiobenzylidene)inden-3-ylmethyl]-N-hydroxy urea Step 1: (Z)-3-Aminomethyl-5-fluoro-2-methyl-1-(4-methylthiobenzylidene)indene To a solution of (Z)-5-fluoro-2-methyl-1-(4-methylthiobenzylidene)inden-3-ylmethyl isocyanate from Example 6, Step 1 in acetic acid (80 mL) there was added 12N aqueous HCl (20 mL); the mixture, which became a suspension, was heated on a steam bath for 15 minutes, then diluted with cold water (150 mL) and filtered. The solid was washed with water and ether to afford the amine hydrochloride (5.1 g) as a yellow solid. The free amine, which is unstable on standing, was liberated just prior to use by neutralization with aqueous 2.5N NaOH and extraction with ethyl acetate to afford the title compound as a dark oil.

Step 2: (Z)-5-Fluoro-3-formyl-2-methyl-1-(4-methylthiobenzylidene)indene

To a suspension of freshly liberated amine from Step 1 (11.5 g, 37 mmol) in ether (220 mL) at 0° C. there was added a solution of t-butyl hypochlorite (4.0 g) in ether (10 mL); the mixture was stirred at 0° C. for 5 minutes as a yellow solid formed. The mixture was then allowed to warm up to room temperature and there was slowly added a solution of potassium tert-butoxide (15 g, 133 mmol) in ethanol (200 mL). The mixture was boiled on a steam bath for 10 minutes and then cooled down. There was added 1N aqueous HCl (200 mL) and after stirring for 20 minutes, the mixture was extracted with ether to afford the crude aldehyde which was purified by column chromatography on silica gel, eluting with a 1:5 mixture of ethyl acetate:hexane. The pure title compound was obtained as an oil.

Step 3: (Z)-5-Fluoro-3-hydroxymethyl-2-methyl-1-(4-methylthiobenzylidene)indene

To a solution of the aldehyde from Step 2 (1.0 g, 3.2 mmol) in ethanol (50 mL) and THF (20 mL) there was added cerous chloride (0.79 g, 3.2 mmol) and sodium borohydride (0.13 g, 3.5 mmol). The mixture was stirred at room temperature for 30 minutes, there was added acetone (3 mL) and after 5 minutes the mixture was diluted with brine (100 mL) and extracted with ether (100 mL). The crude material was purified by column chromatography on silica gel, eluting with a 1:5 mixture of ethyl acetate-hexane to afford the title compound as a thick yellow oil.

Step 4: (Z)-N-[5-Fluoro-2-methyl-1-(4-methylthiobenzylidene)inden-3-ylmethyl]-N-hydroxy urea Following the procedure of Example 3, Method B, Steps 2-5, but substituting the alcohol intermediate from Steps 3 for (Z)-5-fluoro-3-(2-hydroxyethyl)-2-methyl-1-(4-methylthiobenzylidene)-indene as starting material, the title compound was obtained as yellow needles, mp: 173°-176° C. dec. after crystallization from ethyl acetate-hexane.

EXAMPLE 10

(Z)-N-{1-[5-Fluoro-2-methyl-1-(4-methylthiobenzylidene)inden-3-yl]ethyl}-N-hydroxy urea Step 1: (Z)-5-Fluoro-3-(1-hydroxyethyl)-2-methyl-1-(4-methylthiobenzylidene)indene To a solution of aldehyde from Example 9, Step 2 (1.5 g, 4.8 mmol) in THF (25 mL) at 0° C. there was added methyl lithium (1.4M) in ether (3.8 mL, 5.3 mmol) and the mixture stirred at 0° C. for 45 minutes; it was then quenched with saturated aqueous ammonium chloride and extracted with ether to afford crude material which was chromatographed on silica gel to provide the title compound as a reddish syrup.

Step 2: (Z)-5-Fluoro-2-methyl-1-(4-methylthiobenzylidene)-3-[1-((tetrahydropyran-2-yl)-hydroxamino)ethyl]indene To a solution of the alcohol from Step 1 (0.25 g, 0.75 mmol) and O-(tetrahydropyran-2-yl)-hydroxylamine (0.1 g, 0.85 mmol) in methylene chloride (5 mL) at 0° C. there was slowly added trifluoroacetic acid (0.25 mL, 3.2 mmol) and the mixture was stirred at 0° C. for 2.5 hours. After quenching with brine the mixture was extracted with ether to afford the crude title compound which was used as such in the next step.

Step 3: (Z)-5-Fluoro-3-(1-hydroxaminoethyl)-2-methyl-1-(4-methylthiobenzylidene)indene The amine intermediate from Step 2 was heated to 50° C. in methanol (20 mL) containing (1R)-(−)-10-camphorsulfonic acid (200 mg) for 18 hours. After quenching with brine the mixture was extracted with ether (100 mL). The crude material was chromatographed on silica gel eluting with a 1:5 mixture of ethyl acetate-hexane to collect the least polar of the two main components of the mixture. This afforded the title compound as a yellow filmy residue which was taken into the next step.

Step 4: (Z)-N-{1-[5-Fluoro-2-methyl-1-(4-methylthiobenzylidene)inden-3-yl]ethyl}-N-hydroxy urea Following the procedure of Example 3, Method A, Step 5, but substituting the indene intermediate from Step 3 for (Z)-5-fluoro-3-(2-hydroxaminoethyl)-2-methyl-1-(4-methylthiobenzylidene)indene as starting material, the title compound was obtained (49 mg) as a yellow solid, mp: 150°-152° C.

EXAMPLE 11

(Z)-N-{3-[5-Fluoro-2-methyl-1-(4-methylthiobenzylidene) inden-3-yl]propyl}-N-hydroxyurea Step 1 (Z)-5-Fluoro-3-(2-iodoethyl)-2-methyl-1-(4-methylthiobenzylidene)indene To a solution of (Z)-5-fluoro-3-(2-hydroxyethyl)-2-methyl-1-(4-methylthiobenzylidene)indene from Example 3, Method B, Step 1, (9.0 g, 27.6 mmol) and tetrabutylammonium iodide (20.4 g, 55 mmol) in pyridine (4.9 mL, 61 mmol) and methylene chloride (180 mL), cooled to −78° C., there was slowly added trifluoromethane sulfonic anhydride (8 mL, 47.6 mmol). The mixture was stirred at −78° C. for 15 minutes, then at room temperature for one hour. It was then diluted with methylene chloride (200 mL) and washed successively with 10% aqueous sodium thiosulfate, 1N aqueous HCl, saturated sodium bicarbonate, and brine. The crude residue from evaporation of the organic phase was chromatographed on a column of silica gel eluting with a 1:10 mixture of ether-hexane to afford the title compound as a thick yellow oil.

Step 2 (Z)-3-(2-cyanoethyl)-5-Fluoro-2-methyl-1-(4-methylthiobenzylidene)indene

A mixture of the iodide from Step 1 (3.7 g, 8.5 mmol) and potassium cyanide (5.5 g, 85 mmol) in DMF (40 mL) was stirred at room temperature for 45 minutes. There was added water (50 mL) and brine (100 mL) and the mixture was extracted with 1:1 ethyl acetate-hexane (4×100 mL); the combined extracts were washed with water (2×50 mL) and brine (1×50 mL), dried and evaporated. The crude residue was chromatographed on silica gel eluting with a 1:2 mixture of ether-ethyl acetate to afford the title compound as a yellow oil.

Step 3: (Z)-5-Fluoro-3-(2-formylethyl)-2-methyl-1-(4-methylthiobenzylidene)indene To a solution of the nitrile from Step 2 (415 mg, 1.24 mmol) in toluene (4.5 mL) at −78° C. there was added diisobutyl aluminum hydride (1M) in toluene (1.9 mL, 1.9 mmol) and the mixture was stirred at −78° C. for 2 hours; methanol (2 mL) was added and the mixture allowed to warm to room temperature. After partition between ether and water, the residue from evaporation of the organic fraction was chromatographed on silica gel eluting with a 1:2 mixture of ether:hexane to afford the pure title compound as an oil which solidified on standing.

Step 4: (Z)-N-{3-[5-Fluoro-2-methyl-1-(4-methylthiobenzylidene)inden-3-yl]propyl}-N-hydroxy urea Following the procedure of Example 3, Method A, Steps 3-5, but substituting the aldehyde from Step 3 for (Z)-5-fluoro-2-methyl-1-(4-methylthiobenzylidene)inden-3-ylacetaldehyde as starting material, the pure title compound was obtained after chromatography on silica gel, eluting with a 1:30 mixture of methanol:methylene chloride, as a yellow solid, mp: 145°-147° C.

EXAMPLE 12

(Z)-N-{4-[5-Fluoro-2-methyl-1-(methylthiobenzylidene) inden-3-yl]butyl}-N-hydroxy urea Step 1: Dimethyl (Z)-5-fluoro-2-methyl-1-(4-methylthiobenzylidene)inden-3-yl malonate To a suspension of 60% sodium hydride dispersion in oil (550 mg, 13.8 mmol) in DMF (25 mL) at 0° C. there was added dimethyl malonate (1.6 mL, 13.8 mmol) and the mixture was stirred at 0° C. for 1 hour affording a suspension. To this was added a solution of (Z)-5-fluoro-3-(2-iodoethyl)-2-methyl-1-(4-methylthiobenzylidene)indene, from Example 11, Step 1, (2.0 g, 4.6 mmol) in DMF (15 mL) and the mixture stirred at 0° C. as gradually a solution resulted; the mixture was then stirred at room temperature for 6 hours. There was added water and brine and the mixture was extracted 3 times with ether. Combined extracts were washed twice with brine, dried and after evaporation the residue was chromatographed on silica gel eluting with a 1:2 mixture of ether-hexane to afford the title compound as an oil.

Step 2: Methyl (Z)-4-[5-fluoro-2-methyl-1-(4-methylthiobenzylidene)inden-3-yl]butanoate A mixture of the diester from Step 1 (1.5 g, 3.4 mmol), lithium chloride (0.29 g, 6.8 mmol), water (61 ML, 3.4 mmol) and dimethyl sulfoxide (10 mL) was refluxed for 30 minutes. After having been cooled to room temperature, the mixture was diluted with water (50 mL) and brine (50 mL), then extracted with a 1:1 mixture of ether:ethyl acetate (3×50 mL). The combined extracts were washed twice with water, dried and evaporated to a residue which was purified by chromatography on silica gel eluting with a 1:2 mixture of ether-hexane to afford the title compound as an oil.

Step 3: (Z)-N-{4-[5-Fluoro-2-methyl-1-(4-methylthiobenzylidene)inden-3-yl]butyl}-N-hydroxy urea Following the procedure of Example 3, Method A, Steps 2-5, but substituting the ester of Step 2 for methyl (Z)-5-fluoro-2-methyl-1-(4-methylthiobenzylidene)inden-3-ylacetate as starting material, the N-hydroxy urea derivative was obtained. After chromatography on silica gel, eluting with a 1:20 mixture of methanol:methylene chloride, followed by trituration with ether and filtration, the pure title compound was obtained as a yellow solid, mp: 154°-157° C.

EXAMPLE 13

(E)-N-{2-[1-(4-Methylthiobenzylidene)inden-3-yl]ethyl}-N-hydroxy urea

Step 1: Methyl inden-3-ylacetate

Following the procedure of Example 19, Step 2, but substituting 1-indanone for 2-methyl-3-(4-methylthiobenzyl)-1-indanone, there was obtained the title compound as an oil.

Step 2: Methyl (E)-1-(4-methylthiobenzylindene)inden-3-ylacetate

To a solution of methyl inden-3-ylacetate (2 g, 10.6 mmol) in dry THF (20 mL) at −70° C. was added dropwise a solution of LDA in THF (25.7 mL, 0.87M, 2.1 eq.). The resulting orange solution was stirred 30 minutes at −70° C. and then 4-methylthiobenzaldehyde (1.6 mL, 11.7 mmol, 1.1 eq.) was added dropwise. The cooling bath was removed and the reaction mixture was left to warm up to room temperature while a precipitate appeared. The reaction mixture was then quenched with a saturated aqueous solution of ammonium chloride and extracted twice with ethyl acetate. The organic phase was washed twice with 1N aqueous HCl, then with brine and dried over MgSO$_4$ and evaporated to dryness. The residue was dissolved in methanol (5 mL) and a solution of benzyltrimethylammonium hydroxide in methanol (Triton B, 1.4M) (6 mL) was added at room temperature. After 10 minutes the reaction mixture was added to 1N aqueous HCl and extracted with ethyl acetate. The organic layer was treated with ethereal diazomethane, dried over MgSO$_4$ and evaporated to dryness. The residue was chromatographed on silica gel eluting with a 95:5 mixture of hexane-ethyl acetate to afford the title compound, as an oil.

p.m.r (250 MHz, CDCl$_3$): δ 2.5 (s, 3H, SMe), 3.65 (s, 2H, CH$_2$CO), 3.75 (s, 3H, CO$_2$Me), 6.95 (s, 1H), 7.25-7.35 (m, 5H), 7.4 (s, 1H), 7.55 (d, 2H), 7.7 ppm (dd, 1H).

The E-configuration of the product was established via Nuclear Overhauser effect (NOE) experiments.
Step 3: (E)-N-{2-[1-(4-Methylthiobenzylidene)inden-3-yl]ethyl}-N-hydroxy urea Following the procedure of Example 3, Method A, Steps 2-5, but substituting the ester of Step 2 for methyl (Z)-5-fluoro-2-methyl-1-(4-methylthiobenzylidene)inden-3-ylacetate as starting material, the title product was obtained in 17% overall yield, mp: 175°-176° C.

EXAMPLE 14

(E)-N-{2-[1-(2-Furylmethine)inden-3-yl]ethyl}-N-hydroxy urea

Following the procedure of Example 13, Steps 2 and 3, but substituting 2-furaldehyde for 4-methylthiobenzaldehyde as starting material, the title product was obtained in 22% overall yield, m.p. 140°-141° C.

EXAMPLE 15

(E)-N-(2-[1-(2-Thienylmethine)inden-3-yl]ethyl)-N-hydroxy urea

Following the procedure of Example 13, Steps 2 and 3 but substituting 2-thiophene carboxaldehyde for 4-methylthiobenzaldehyde as starting material, the title product was obtained in 18% overall yield, mp: 145° C.

Analysis: Calc'd for C$_{17}$H$_{16}$O$_2$N$_2$S: C, 65.37; H, 5.17; S, 10.24; N, 8.97. Found: C, 65.25; H, 5.30; S, 10.11; N, 8.85.

EXAMPLE 16

(Z)-N-{2-[3-Methyl-1-(4-methylthiobenzylidene)inden-2-yl]ethyl}-N-hydroxy urea

Step 1: 1-Methyl-3-oxo-2-indenylidene acetic acid

A mixture of 3-methylindan-1-one (J.C.S. Chem. Comm. 1973, 636) (2.0 g, 13.7 mmol), glyoxylicacid hydrate (12.6 g, 137 mmol), dioxane (96 mL) and sulfuric acid (8.2 mL) was stirred at 95° C. for 45 minutes. Water (100 mL) was added, and the dioxane evaporated. The residual aqueous suspension was diluted with water and filtered to afford the title compound as a yellow solid.

Step 2: Methyl 1-methyl-3-oxo-2-indenylidene acetate

To a solution of the acid from Step 1 (1.25 g, 6.2 mmol) in methanol (20 mL) there was slowly added thionyl chloride (1.1 g, 9.3 mmol) and the mixture stirred at room temperature for 22 hours. On concentration to a small volume, a solid crystallized out and was filtered to afford the title ester as light yellow crystals, mp: 96°-97° C.

Step 3: Methyl (Z)-3-methyl-1-(4-methylthiobenzylidene)inden-2-ylacetate

To a solution of the ester from Step 2 (560 mg, 2.6 mmol) in ether (5 mL) at 0° C. was added a solution in ether of 4-methylthiobenzylmagnesium chloride (0.21M, 13.6 mL, 1.1 eq). After complete addition, acetic acid (0.2 mL) was added followed by an aqueous solution of ammonium chloride. The reaction mixture was extracted with ethyl acetate and the organic layer was washed with brine, dried over MgSO$_4$ and evaporated to dryness. The crude material was stirred for 2 h at 50°-60° C. with a mixture of acetic acid: water: 12N HCl, 10:1:3 (8 mL). Water was added and the reaction mixture was extracted with ethyl acetate. The organic layer was washed with brine, dried over MgSO$_4$ and evaporated. The crude product was chromatographed on silica gel eluting with a 1:9 mixture of ethyl acetate:hexane to afford the title compound as an oil.

p.m.r (250 MHz, CDCl$_3$): δ 2.2 (s, 3H, vinylic CH$_3$), 2.55 (s, 3H, SMe), 3.6 (s, 2H, CH$_2$CO), 3.7 (s, 3H, CO$_2$CH$_3$), 6.8-7.7 ppm (m, 9H).

Step 4: (Z)-2-(2-Hydroxyethyl)-3-methyl-1-(4-methylthiobenzylidene)indene

To a solution of the ester from Step 3 (270 mg, 0.83 mmol) in dry THF (5 mL) at 0° C. was added a solution of diisobutyl aluminum hydride (1M) in toluene (2.1 mL, 2.1 mmol, 3.5 eq). After 1 hour, the reaction mixture was added dropwise to a solution of 1N aqueous HCl and extracted with ethyl acetate. The organic phase was washed with brine, dried over MgSO$_4$ and evaporated to dryness. The crude product was chromatographed on silica gel eluting with a 1:3 mixture of ethyl acetate-hexane to afford pure title compound as a yellow oil.

p.m.r (250 MHz, CDCl$_3$); δ 2.2 (s, 3H, vinylic CH$_3$), 2.55 (s, 3H, SMe), 2.9 (t, 2H, J=7 Hz, CH$_2$), 3.8 (t, 2H, J=7 Hz, CH$_2$), 6.95 (m, 1H), 7.1 (s, 1H), 7.2-7.3 (m, 4H), 7.45 ppm (d, 3H).

Step 5: (Z)-3-Methyl-1-(4-methylthiobenzylidene)indene-2-ylacetaldehyde

A solution of the primary alcohol from Step 4 (1 g, 3.25 mmol) in dichloromethane (10 mL) was added dropwise to a mixture of chromium trioxide (3.3 g, 32 mmol, 10 eq.) in dichloromethane (50 mL) at 0° C. containing pyridine (5.1 mL, 63 mmol, 20 eq.). After 1.5 hour, ether was added to precipitate the chromium salts and the heterogenous mixture was filtered through silica gel and washed with ether. After evaporation to dryness, the residue was purified by chromatography on silica gel eluting with a 15:85 mixture of ethyl acetate-hexane to yield the title compound as a yellow oil.

p.m.r. (250 MHz, CDCl$_3$): δ 2.2 (s, 3H, vinylic CH$_3$, 2.5 (s, 3H, SCH$_3$), 3.6 (d, 2H, J=2.5 Hz, CH$_2$CO), 7.0 (m), 7.3 (m), 7.45 (dd, J=11, 7.5 Hz), 7.8 (d, J=9 Hz), 9.7 ppm (t, 1H, CHO).

Step 6: (Z)-N-{2-[3-Methyl-1-(4-methylthiobenzylidene)-inden-2-yl]ethyl}-N-hydroxy urea Following the procedure of Example 3, Method A, Steps 3-5, but substituting the aldehyde of Step 5 for (Z)-5-fluoro-2-methyl-1-(4-methylthiobenzylidene)inden-3-ylacetaldehyde as starting material, the title compound was obtained, mp: 120°-122° C.

EXAMPLE 17

(Z)-N-{2-[3-Methyl-1-(4-methylsulfinylbenzylidene)inden-2-yl]ethyl}-N-hydroxy urea Step 1 (Z)-2-(2-hydroxaminoethyl)-3-methyl-1-(4-methylsulfinylbenzylidene)indene To a solution of the hydroxylamine from Example 16, Step 6 (130 mg, 0.40 mmol) in dichloromethane (5 mL) at 0° C. was added in one portion 85% m-chloroperoxy benzoic acid (90 mg, 0.44 mmol, 1.1 eq.). After 45 minutes the reaction mixture was diluted with dichloromethane and washed successively with 1N aqueous sodium hydroxide, water, brine, dried over $MgSO_4$ and evaporated to dryness. The residue was chromatographed on silica gel eluting with a 30:1 mixture of dichloromethane:methanol to yield the title compound as a yellow oil.

Step 2 (Z)-N-}2-[3-Methyl-1-(4-methylsulfinylbenzylidene)inden-2-yl]ethyl}-N-hydroxy urea Following the procedure of Example 3, Method A, Step 5, but substituting the hydroxylamine of Step 1 for (Z)-5-fluoro-3-(2-hydroxaminoethyl)-2-methyl-1-(4-methylthiobenzylidene)indene as starting material, the N-hydroxy urea derivative was obtained. After chromatography on silica gel eluting with a 5:95 mixture of methanol:methylene chloride, the pure title compound was obtained in 91% yield, mp: 166°–169° C.

EXAMPLE 18

(Z)-N-{2-[3-Methyl-1-(4-methylsulfonylbenzylidene)inden-2-yl]ethyl}-N-hydroxy urea Step 1: Methyl (Z)-3-methyl-1-(4-methylsulfonylbenzylidene)inden-2-ylacetate To a solution of methyl (Z)-3-methyl-1-(4-methylthiobenzylidene) indene-2-yl acetate from Example 16, Step 3, (1 g, 3.1 mmol) in dichloromethane (30 mL) at 0° C. was added in one portion 85% m-chloroperoxy benzoic acid (1.6 g, 7.7 mmol, 2.5 eq.). The reaction mixture was stirred at 0° C. for 30 minutes, then diluted with dichloromethane and washed successively with an aqueous solution of 1N sodium hydroxide, brine, dried over $MgSO_4$ and evaporated to dryness. The crude product was purified by flash chromatography eluting with a 65:35 mixture of hexane-ethyl acetate to afford the title compound.

p.m.r (250 MHz, $CDCl_3$): δ 2.2 (s, 3H, vinylic $CH_3$), 3.15 (s, 3H, $SO_2CH_3$), 3.6 (s, 2H, $CH_2CO$), 3.7 (s, 3H, $CO_2CH_3$), 6.95 (m, 1H), 7.1 (s, 1H), 7.15–7.3 (m, 3H), 7.75 (d, 2H, J=7.5 Hz), 8.8 ppm (d, 2H, J=7.5 Hz).

Step 2 (Z)-N-{2-[3-Methyl-1-(4-methylsulfonylbenzylidene)inden-2-yl]ethyl}-N-hydroxy urea Following the procedure of Example 3, Method A, Steps 2–5, but substituting the ester from Step 1 for (Z)-5-fluoro-2-methyl-1-(4-methylthiobenzylidene) inden-3-ylacetate as starting material, the title compound was obtained in 27% overall yield, mp: 140°–142° C.

EXAMPLE 19

N-{2-[2-Methyl-1-(4-methylthiobenzyl)inden-3-yl]ethyl}-N-hydroxy urea

Step 1: 2-Methyl-3-(4-methylthiobenzyl)-1-indanone

To a cooled solution (−70° C.) of LDA (1M) in THF (37 mL) was added dropwise a solution of 2-methyl-1-indanone (J.A.C.S. Vol. 98, 8119–8124 (1976)) (2.5 g, 17 mmol) in THF (20 mL). The resulting dark red solution was stirred at room temperature for 3 hours, then cooled to −20° C. and a solution of 4-methylthiobenzyl chloride (3.1 g, 18 mmol) in THF (15 mL) was added slowly. The addition completed, the reaction mixture was stirred at −20° C. for 30 minutes before being quenched with 3N aqueous HCl (50 mL) and brine (50 mL). The product was extracted with ether, dried over $MgSO_4$ and evaporated to dryness. The oily residue was chromatographed on silica gel eluting with a 1:5 mixture of ethyl acetate-hexane to afford the pure title compound as an oil.

Step 2: Methyl 2-methyl-3-(4-methylthiobenzyl)inden-1-ylacetate

To a solution of the indanone derivative from Step 1 (885 mg, 3.14 mmol) in ether (20 mL) were added successively zinc (840 mg, 12.8 mmol), methyl bromoacetate (0.5 mL, 5 mmol) and iodine (200 mg). The reaction mixture was refluxed for 3 hours, then cooled to 0° C. and 6N aqueous HCl was added dropwise until the zinc complex was completely decomposed. The organic layer was decanted, washed with brine, dried over $Na_2SO_4$ and evaporated to dryness. The oily residue was dissolved in formic acid and evaporated to dryness to complete the dehydration of the intermediate methyl [1-hydroxy-2-methyl-3-(4-methylthiobenzyl)indan-1-yl]acetate. The resulting oily residue was chromatographed on silica gel eluting with a 1:19 mixture of ethyl acetate-hexane to afford pure title compound as an oil.

Step 3: N-{2-[2-Methyl-1-(4-methylthiobenzyl)inden-3-yl]ethyl}-N-hydroxy urea

Following the procedure of Example 3, Method A, Steps 2–5, but substituting the ester from Step 2 for methyl (Z)-5-fluoro-2-methyl-1-(4-methylthiobenzylidene)inden-3-ylacetate as starting material, the title compound was obtained in 44% overall yield, mp: 163°–164° C.

Analysis: Calc'd for $C_{21}H_{24}N_2O_2S$: C, 68.45; H, 6.56; N, 7.60; S, 8.70. Found: C, 68.22; H, 6.85; N, 7.30; S, 8.55.

EXAMPLE 20

N-[2-(1-Ethylinden-3-yl)ethyl]-N-hydroxy urea

Step 1: Methyl (1-ethylinden-3-yl)acetate

To a solution of methyl inden-3-ylacetate from Example 13, Step 1 (1 g, 5.32 mmol) in THF (10 mL) at −70° C. was added dropwise a solution of LDA (12.2 mL, 0.87M, 2 eq.) in THF. The resulting orange solution was stirred for 30 minutes at −70° C. and then ethyl iodide (0.47 mL, 5.85 mmol) was added dropwise. The cooling bath was removed and the reaction mixture was left to warm to room temperature while a precipitate appeared. The reaction mixture was then quenched with a saturated aqueous solution of ammonium chloride and extracted with ethyl acetate. The organic layer was washed with 1N HCl, then with brine, dried over $MgSO_4$ and evaporated to dryness. The oily residue was chromatographed on silica gel eluting with a 1:19 mixture of ethyl acetate-hexane to afford pure title compound as an oil.

Step 2: N-[2-(1-ethylinden-3-yl)ethyl]-N-hydroxy urea

Following the procedure of Example 3, Method A, Steps 2–5, but substituting the ester of Step 1 for methyl (Z)-5-fluoro-2-methyl-1-(4-methylthiobenzylidene)inden-3-ylacetate as starting material, the title compound was obtained in 66% overall yield, mp: 81°–83° C.

Analysis: Calc'd for $C_{14}H_{18}N_2O_2$: C, 68.25; H, 7.37; N, 11.38. Found: C, 68.29; H, 7.50; N, 11.09.

What is claimed is:

1. A compound of the formula I:

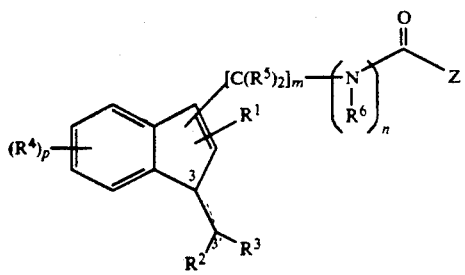

wherein:
$R^1$ and $R^5$ are independently:
  a) hydrogen;
  b) lower alkyl;
$R^2$ and $R^3$ are independently
  c) hydrogen;
  d) lower alkyl;
  e) phenyl substituted with c)–d) hereinabove or $R^7$; where $R^7$ is —$OR^8$, —$SR^9$, —$S(O)_2R^9$, —CN, —$CO_2R^8$, or halogen;
    wherein $R^8$ is hydrogen or $R^9$;
    $R^9$ is lower alkyl;
  f) heteroaryl substituted with c)–d) hereinabove or $R^7$;
  g) lower alkyl monosubstituted with e) to f) hereinabove;
R4 is hydrogen, lower alkyl, lower alkynyl, lower alkenyl, —$OR^8$, —$C(O)R^8$, —$NO_2$, $N(R^8)_2$, —$NR^8C(O)R^8$, —$R^{10}N(R^8{}_2)$, $SO_2N(R^8)_2$, —$SR^9$, —$R^{10}OH$, —$S(O)_2R^9$, —CN, —$CO_2R^8$, —$CON(R^8)_2$, halogen, cycloalkyl, —$R^{10}$—halogen, or cycloalkoxy; where $R^8$ and $R^9$ are defined hereinabove and $R^{10}$ is lower alkyl;
$R^6$ is hydrogen or OM;
M is hydrogen, a pharmacetically acceptable cation or —$C(O)R^{11}$;
  where $R^{11}$ is lower alkyl, or phenyl substituted with hydrogen, lower alkyl or $R^7$;
m is 1 to 4;
n is 0 or 1;
p is 0 to 2;
Z is lower alkyl or $NR^{12}R^{13}$; where $R^{12}$ is —OM or $R^{13}$; $R^{13}$ is hydrogen, lower alkyl or $R^{12}$ and $R^{13}$ are joined to form a heterocyclic ring of 3 to 6 carbon atoms and 1 or 2 heteroatoms selected from N, S or O, provided that $R^{12}$ is —OM when $R^6$ is hydrogen or n is 0;
and the dotted line between positions 3 and 3' indicates an optional double bond;
and the pharmaceutically acceptable salts thereof.

2. The compound according to claim 1 which is:
(Z)-N-hydroxy-N-methyl-5-fluoro-2-methyl-1-(4-methylthiobenzylidene)inden-3-ylacetamide,
(Z)-N-{2-[5-fluoro-2-methyl-1-(4-methylthiobenzylidene)inden-3-yl]ethyl}-N-hydroxyacetamide,
(Z)-N-{2-[5-fluoro-2-methyl-1-(4-methylthiobenzylidene)inden-3-yl]ethyl}-N-hydroxyurea,
(Z)-N-{2-[5-fluoro-2-methyl-1-(4-methylthiobenzylidene)inden-3-yl]ethyl}-N-hydroxy-N'-methylurea,
(Z)-N-{2-[5-fluoro-2-methyl-1-(4-methylthiobenzylidene)inden-3-yl]ethyl}-N-hydroxy-N'-t-butylurea,
(Z)-N-[5-fluoro-2-methyl-1-(4-methylthiobenzylidene)inden-3-ylmethyl]-N'-hydroxy-N'-methyl urea,
(Z)-N-{2-[5-fluoro-2-methyl-1-(4-methylsulfinylbenzylidene)inden-3-yl]ethyl}-N-hydroxy urea,
(Z)-N-{2-[5-fluoro-2-methyl-1-(4-methylsulfonylbenzylidene)inden-3-yl]ethyl}-N-hydroxy urea,
(Z)-N-[5-fluoro-2-methyl-1-(4-methylthiobenzylidene)inden-3-ylmethyl]-N-hydroxy urea,
(Z)-N-{1-[5-fluoro-2-methyl-1-(4-methylthiobenzylidene)inden-3-yl]ethyl}-N-hydroxy urea,
(Z)-N-{3-[5-fluoro-2-methyl-1-(4-methylthiobenzylidene)inden-3-yl]propyl}-N-hydroxy urea,
(Z)-N-{4-[5-fluoro-2-methyl-1-(4-methylthiobenzylidene)inden-3-yl]butyl}-N-hydroxy urea,
(E)-N-{2-[1(4-methylthiobenzylidene)inden-3-yl]ethyl}-N-hydroxy urea,
(E)-N-{2-[1-(2-furylmethine)inden-3yl]ethyl}-N-hydroxy urea,
(E)-N-{2-[1-(2-thienylmethine)inden-3-yl]ethyl}-N-hydroxy urea,
(Z)-N-{2-[3-methyl-1-(4-methylthiobenzylidene)inden-2-yl]ethyl}-N-hydroxy urea,
(Z)-N-{2-[3-methyl-1-(4-methylsulfinylbenzylidene)inden-2-yl]ethyl}-N-hydroxy urea,
(Z)-N-{2-[3-methyl-1-(4-methylsulfonylbenzylidene)inden-2-yl]ethel}-N-hydroxy urea,
N-{2-[2-methyl-1-(4-methylthiobenzyl)inden-3-yl]ethyl}-N-hydroxy urea or
N-[2-(1-ethylinden-3-yl)ethyl]-N-hydroxy urea.

3. A compound of the formula Ia wherein the substituents are as follows:

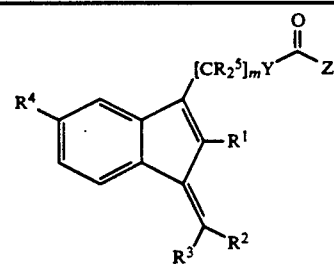

| $[CR_2{}^5]_m$ | Y | Z | $R^1$ | $R^2$ | $R^3$ | $R^4$ |
|---|---|---|---|---|---|---|
| $CH_2$ | — | $N(OH)CH_3$ | $CH_3$ | H | $C_6H_4$-4-$SCH_3$ | F, |
| $(CH_2)_2$ | NOH | $CH_3$ | $CH_3$ | H | $C_6H_4$-4-$SCH_3$ | F, |
| $(CH_2)_2$ | NOH | $NH_2$ | $CH_3$ | H | $C_6H_4$-4-$SCH_3$ | F, |
| $(CH_2)_2$ | NOH | $NHCH_3$ | $CH_3$ | H | $C_6H_4$-4-$SCH_3$ | F, |
| $(CH_2)_2$ | NOH | $NH(CH_3)_3$ | $CH_3$ | H | $C_6H_4$-4-$SCH_3$ | F, |

-continued

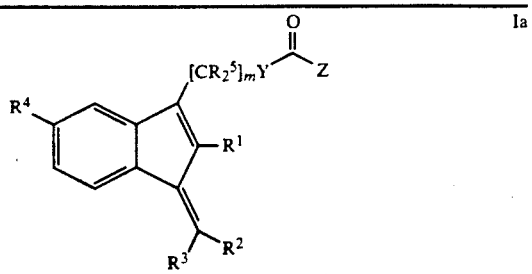

| [CR$_2^5$]$_m$ | Y | Z | R$^1$ | R$^2$ | R$^3$ | R$^4$ |
|---|---|---|---|---|---|---|
| CH$_2$ | NH | N(OH)CH$_3$ | CH$_3$ | H | C$_6$H$_4$-4-SCH$_3$ | F, |
| (CH$_2$)$_2$ | NOH | NH$_2$ | CH$_3$ | H | C$_6$H$_4$-4-S(O)CH$_3$ | F, |
| (CH$_2$)$_2$ | NOH | NH$_2$ | CH$_3$ | H | C$_6$H$_4$-4-S(O)$_2$CH$_3$ | F, |
| CH$_2$ | NOH | NH$_2$ | CH$_3$ | H | C$_6$H$_4$-4-SCH$_3$ | F, |
| CHCH$_3$ | NOH | NH$_2$ | CH$_3$ | H | C$_6$H$_4$-4-SCH$_3$ | F, |
| (CH$_2$)$_3$ | NOH | NH$_2$ | CH$_3$ | H | C$_6$H$_4$-4-SCH$_3$ | F, |
| (CH$_2$)$_4$ | NOH | NH$_2$ | CH$_3$ | H | C$_6$H$_4$-4-SCH$_3$ | F, |
| (CH$_2$)$_2$ | NOH | NH$_2$ | H | C$_6$H$_4$-4-SCH$_3$ | H | H, |
| (CH$_2$)$_2$ or | NOH | NH$_2$ | H | C$_4$H$_3$O* | H | H |
| (CH$_2$)$_2$ | NOH | NH$_2$ | H | C$_4$H$_3$S** | H | H |

*2-FURYL
**2-THIENYL

4. A compound of the Formula Ib:

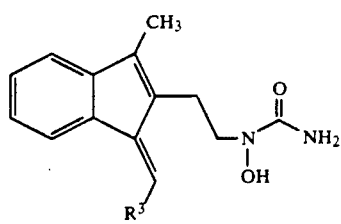

wherein:
R$^3$ is:
a) hydrogen;
b) lower alkyl;
c) phenyl substituted with a)-b) hereinabove or R$^7$;
where R$^7$ is —OR$^8$, —SR$^9$, —S(O)$_2$R$^9$, —CN, —CO$_2$R$^8$, or halogen;
wherein R$^8$ is hydrogen or R$^9$;
R$^9$ is lower alkyl;
d) heteroaryl substituted with c)-d) hereinabove or R$^7$;
e) lower alkyl monosubstituted with c) to d) hereinabove.

5. A compound of the Formula Ic:

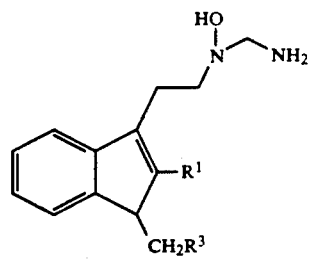

wherein:
R$^1$ is:
a) hydrogen;
b) lower alkyl;
R$^3$ is:
c) hydrogen;
d) lower alkyl;

e) phenyl substituted with c)-d) hereinabove or R$^7$;
where R$^7$ is —OR$^8$, —SR$^9$, —S(O)$_2$R$^9$, —CN, —CO$_2$R$^8$, or halogen;
wherein R$^8$ is hydrogen or R$^9$;
R$^9$ is lower alkyl;
f) heteroaryl substituted with c)-d) hereinabove or R$^7$;
g) lower alkyl monosubstituted with e) to f) hereinabove.

6. A pharmaceutical composition comprising a therapeutically effective amount of a compound of claim 1 and a pharmaceutically acceptable carrier.

7. The pharmaceutical composition of claim 6 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; H$_2$-receptor antagonists; antihistaminic agents; prostaglandin antagonists; thromboxane antagonists; thromboxane synthetase inhibitors; and ACE antagonists.

8. A pharmaceutical composition according to claim 7, wherein the second active ingredient is a non-steroidal anti-inflammatory drug.

9. A pharmaceutical composition of claim 8, wherein the weight ratio of said compound of claim 1 to said second active ingredient ranges from about 1000:1 to 1:1000.

10. A method of preventing the synthesis, the action, or the release of SRS-A or leukotrienes in a mammal which comprises administering to said mammal an effective amount of a compound of claim 1.

11. The method of claim 10 wherein the mammal is man.

12. A method of treating asthma in a mammal comprising administering to a mammal in need of such treatment a therapeutically effective amount of a compound of claim 1.

13. A method of treating inflammatory diseases of the eye in a mammal which comprises administering to a mammal in need of such treatment a therapeutically effective amount of a compound of claim 1.

14. The method of claim 13 wherein the mammal is man.

* * * * *